United States Patent [19]

Koch et al.

[11] Patent Number: 4,531,409

[45] Date of Patent: Jul. 30, 1985

[54] TEST SYSTEM FOR DEFECT DETERMINATION IN WELDING SEAMS

[75] Inventors: Friedrich-Otto Koch, Unna Massen; Hans-Jürgen Wahl, Münster, both of Fed. Rep. of Germany

[73] Assignee: Hoesch Werke Aktiengesellschaft, Dortmund, Fed. Rep. of Germany

[21] Appl. No.: 416,082

[22] Filed: Sep. 8, 1982

[30] Foreign Application Priority Data

Sep. 10, 1981 [DE] Fed. Rep. of Germany ... 8126298[U]

[51] Int. Cl.³ .............................................. G01N 29/04
[52] U.S. Cl. ........................................ 73/588; 73/602; 73/622; 73/638
[58] Field of Search ................... 73/602, 622, 638, 588

[56] References Cited

U.S. PATENT DOCUMENTS

| 3,332,278 | 7/1967 | Wood et al. | 73/602 |
| 3,411,344 | 11/1968 | Lloyd | 73/622 |
| 3,868,847 | 3/1975 | Gunkel | 73/622 |
| 3,996,791 | 12/1976 | Niklas et al. | 73/622 |
| 4,055,989 | 11/1977 | Henry et al. | 73/638 |

Primary Examiner—Anthony V. Ciarlante
Attorney, Agent, or Firm—Horst M. Kasper

[57] ABSTRACT

A system for non-destructive testing of metallic materials and for, in particular, welding seams. An ultrasonic sensor is employed and ultrasonic defect signals are producted according to the pulse echo method. The ultrasonic defect signals are digitized and the digitized signals are combined with signals corresponding to longitudinal positions along the welding seam. A defect curve is produced form the data resulting from combining the digitized signals with the signals corresponding to longitudinal positions along the welding seam. The resulting defect curve is compared with data from a catalog of classes of defects. The system eliminates the need for manual ultrasonic reinspection of presumed welding defects.

11 Claims, 2 Drawing Figures

TEST SYSTEM FOR DEFECT DETERMINATION IN WELDING SEAMS

BACKGROUND OF THE INVENTION

1. Field of the Invention

The present invention relates a a system for locating and identifying of defects in metallic materials and in particular in welding seams employing ultrasonic pulse-echo method.

2. Brief Description of the Background of the Invention Including Prior Art

As is known in general only the peak defect signal is employed for evaluating a defect in the ultrasonic flaw detection of welding seams according to the pulse-echo method. However, the result does not coincide with the extent of the damage of the defect as it relates to the final product, in particular in view of interferences there is no one to one correlation between the ultrasonic defect signal and the depth of the defect and therefor, the evaluation of an individual ultrasonic defect signal in this manner is open to serious questions.

For this reason, up to now in general there was required an manual ultrasonic reinspection of suspected defect locations resulting in requirements seriously interfering with a substantially automated production process.

On the other hand there is known a defect size determination, in particular in the evaluation of defects in the ultrasonic testing of sheet metals (J. and H. Krautkramer, Werkstoffprufung mit Ultraschall, Springer-Verlag, Publisher 1975, pages 401 to 415, and Robert C. McMaster, Nondestructing Testing Handbook, New York, 1963 Section 45-24 to 45-26 "Contour of Discontinuities".), where based on the size and frequency of material flaws a quality decision appropriate to the final product can be performed by class comparison according for example to the German delivery standards "Stahl-Eisen-Lieferbedingungen 072" or similarly according to ASTME 435-75 or, respectively ASTME 578-716. In this case there registration of the defects can be provided by recording and the evaluation can be done virtually or by way of a computer. Such a simple determination of the defect surfaces is not possible in the case of welding seams, since in this situation the defects are substantially vertical with respect to the surface of the metal piece and therefor, the usual ultrasonic transmission method cannot be employed.

SUMMARY OF THE INVENTION

1. Purposes of the Invention

It is an object of the present invention to provide an improved test procedure for defect testing of welding seams according to an ultrasonic pulse-echo method.

It is another object of the present invention to provide a method for non-destructive testing of welding seams where the extent of a defect or flaw is probed and where by employing of commercial test equipment in automatic production processes a classification of welding seam flaws is made possible in view of a classification based on the intended uses of the metal pieces.

It is a further object of the present invention to provide an apparatus for testing metallic materials at their welding seams providing length parameters as to the location of flaws and providing size parameters as to the extent of a flaw in the welding seam.

These and other objects and advantages of the present invention will become evident from the description which follows.

3. Brief Description of the Invention

The present invention provides a method for nondestructive testing of metallic materials which comprises testing a welding seam with ultrasonic equipment, sensing ultrasonic defect signals according to the pulse-echo method, digitizing ultrasonic defect signals, and combining the digitized signals with signals corresponding to longitudinal positions along the welded seam. Preferably a defect curve is produced from the data resulting from combining the digitized signals with signals corresponding to logitudinal positions along the welding seam. The data resulting from combining digitized signals with signals corresponding to longitudinal position along the welding seam can be compared with data from a provided catalog of classes of defects in metal materials. When comparing the data a threshold can be provided for the defect signals.

The metallic material can be marked if a threshold value is exceeded by defect signal from the ultrasonic data. In addition, the magnetic stray flux can be used for sensing defect signals corresponding to depth of the defects. The length, over which a defect signal is observed, can be determined versus the length, over which no defect signal is observed.

Furthermore, the length over which a defect signal is observed, can be compared with the n-fold of the length, over which no defect signal is observed. The length, over which a defect signal is observed, can be added to the proceding length over which a defect signal was observed. These steps can be repeated with the generated total length to be considered, over which defects are observed, until a larger length, over which no defect signals are observed occurs, where n can assume the values 0.5, 1, 2, 3, 4, . . . x; where x is an integer.

The lengths over which defects are observed can be correlated for uncovering the presence of periodicity along the extension of the metal material and the resulting correlations can be compared with a preselected stored catalog of periods.

There is also provided a testing apparatus for metallic materials having welding seams according to one aspect of the present invention, which comprises sensing means for providing length pulses upon passage over certain length intervals along a metallic material by the sensing means, a shift register connected to the sensing means for shifting length-pulses coming from the sensing means; an electrically activated ultrasonic transducer coupled to the metallic material for transferring ultrasonic power to the metallic material, an ultrasonic receiver connected to the transducer for receiving ultrasonic signals, an analog-digital converter connected to the ultrasonic receiver, a peak signal storage connected to the analog digital converter, a digital processor connected to the peak signal storage and to the shift register for summing the signal-length interval products to provide defect integrals, a comparator connected to the digital processor for comparing defect integrals with preselected values, and a memory connected to the correlator.

Preferably, the testing apparatus can employ a sensing wheel as a sensing means a calculating provision can be connected to the memory.

The novel features, which are considered as characteristic for the invention, are set forth in particular in the appended claims. The invention itself, however, both as to its construction and its method of operation, together with additional objects and advantages thereof, will be best understood from the following description of specific embodiments when read in connection with accompanying drawings.

BRIEF DESCRIPTION OF THE DRAWING

In the accompanying drawing, in which is shown one of the various possible embodiments of the present invention.

FIG. 1 is a view of a schematic block circuit diagram representing the system of the present invention;

DESCRIPTION OF INVENTION AND PREFERRED EMBODIMENTS

Figure 1:
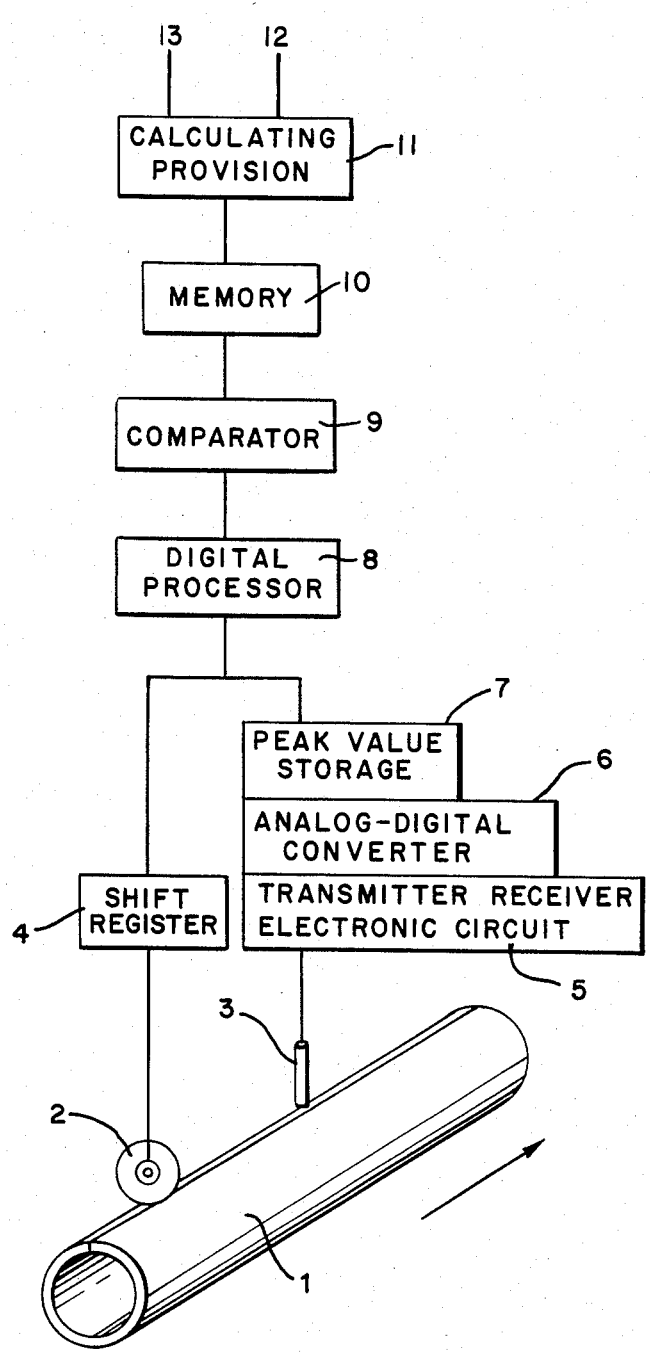
FIG. 1 is a view of a schematic block

In accordance with the present invention an improved system is provided for testing and evaluation of ultrasonic signals, which goes beyond the conventional step of determining a peak amplitude versus a testing threshold. The present system provides for recognizing the flaws in welding seams according to their actual potential of damage, and in particular regarding their longitudinal and depth extension.

The testing is performed according to the ultrasound pulse-echo method. The resulting ultrasound defect signals are digitized and correlated by calculation to a signal defect integral area composed of bar-shaped integral elements in connection with signals from a lengths-pick-up for the corresponding section of the metallic material piece. After classification the integrals can be compared by calculation with catalogs of defect integrals and defective metal material pieces can be sorted out.

In addition or in place of the digitized ultrasonic defect signals also the digitized defect signals from the magnetic stray flux test can be employed for the calculation and correlation to determine the integrals of the defect signals.

The system of the present invention can be applied to the non-destructive testing of metallic work pieces, where the length of the metal piece can be correlaterd with an ultrasonic test result for determining defect integrals coordinated to the position on the metal piece. The determined integral can be classified and compared with a catalog of classes for the flaw determination in welding seams according to the ultrasonic pulse-echo method and according to the magnetic stray flux test in order to obtain the defect integrals.

Thus in accordance with the present invention welding seam flaws can be much more differentially evaluated as compared with the conventional methods, since now the possibility is provided to take into consideration the length of defects and the extent of defects, which are of decisive importance for fracture mechanics according to the state of the art.

In the evaluation of flaws according to their signal defect integral area also the initially described disadvantage of the evaluation of individual ultrasonic defect signals is substantially averaged, since natural defects in general show small angle changes in their course, which result in a substantial weakening of the interference holes and peaks. A special evaluation of the gaps between two signal defect integral areas aids in correspondingly weighting the importance of accumulated small defects or respectively to eliminate the recited interference holes from the evaluation.

The above described classification of the defects with the usual test speeds of about 60 meters per minute and the defect extensions to be expected of from about 0.5 mm into the region of decimeters can be performed particularly easily if initially the digitized ultrasonic defect signals are processed in a commercial microcomputer including an integrated comparator. This way it is also possible to find periodically occurring defects such as for example generated by a surface damaged roll in a roller mill and to compare with a digitally memorized catalog of possible defect periods, in order to allow to make a distinction between various defects.

Some types of defects and in particular their defect depths as is known can be easier determined by way of the magnetic stray flux method. This knowledge is incorporated in a further feature of the invention testing system, where the ultrasonic testing is combined with the magnetic stray flux test, which is particularly advantageous for determining the amplitude height of the signal defect integrals. Equipment for performing the magnetic stray flux method is commercially available, for example from Firm Foerster, 7410 Reutlingen, West Germany. Combining the ultrasonic testing according to the invention with the stray flux method allows to probe better the depth of the defects.

The invention system allows to achieve an improvement in the evaluation of defects to such an extent that in the future a manual reexamination will become superfluous. The invention is not limited to the testing of welding seams, but can also be applied to other areas of metallic materials evaluation such as for example the testing of cracks in metal pieces.

Referring now to FIG. 1, there is shown a steel tube 1 having a welding seam running parallel to the tube axis at one side and an ultrasonic sensor 3. The steel tube is moved in its axial direction at a speed of 54 meters per minute below the ultrasonic sensor. The sensing wheel 2 with a pulse generator for intervals of 0.3 mm measures the tube length running through. The pulse sequence from the sensing wheel can be from about 10 to 10000 per second.

A shift register 4 provided for appropriate longitudinal position coupling of longitudinal pulses and of ultrasonic defect signals. Preferably the amount of shifting corresponds to the distance between the sensing wheel and the ultrasonic sensor. The shifting length can amount to several meters, for example by the distance between the point of the ultrasonic measurement and the marking device for marking the defects. The shift register provided that where the measurements point and marking point cannot be disposed at the same place, for example to avoid contamination of the measurement apparatus with paint, nevertheless the defect will be marked according to its position.

In general the ultrasonic sensor comprises a transducer and a receiver. Such ultrosonic equipment is commercially available, for example from Magnaflux Corporation. The frequency of the ultrasonic waves employed can range from about 0.5 to 20 megacycles and preferably from about 1 to 5 magacycles. The transducer transmits ultrasonic waves into the metallic materials and also receives the reflected waves.

Figure 2:
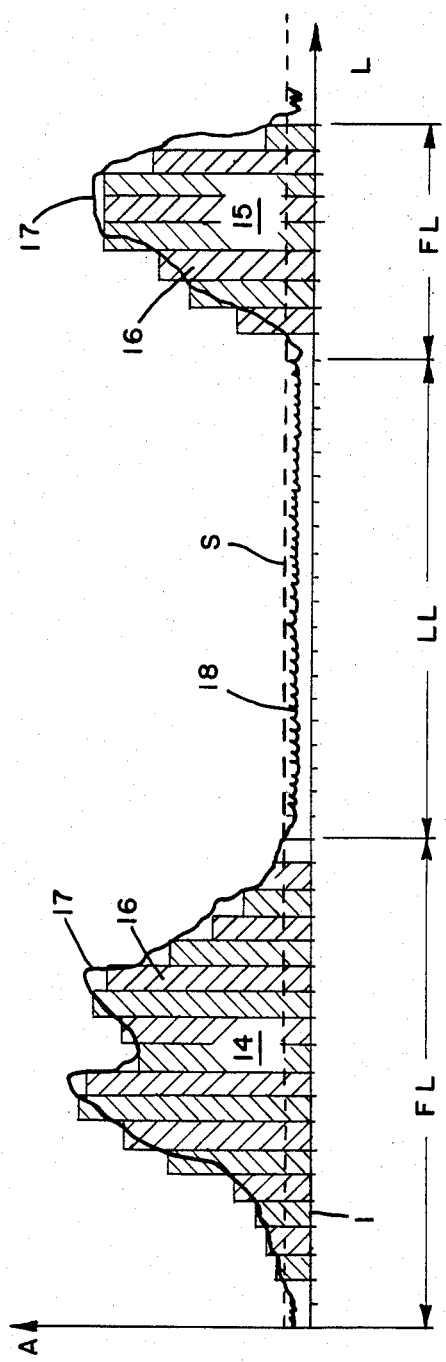
FIG. 2 is a view of graph representing the determination of the defect integrals from length and ultrasonic measurements.

The ultrasonic defect signals pass from a transmitter-receiver electronic circuit 5 via an analog-digital converter 6 to a peak value storage 7, which transfers only the maximum digitized ultrasonic defect signal per unit of length into the digital processor 8 for providing multiplication of the length intervals with the signal amplitudes and then adding the product, which is a signal-length interval product 16, to the possible previously determined preceding defect signal integral elements to a signal defect integral 14 as shown in FIG. 2. Since the length of the gap LL at the defect threshold level S is larger than the length of defect interval FL, the determined signal defect integral 14 is compared with previously provided set point from amplitude-dependent, staggered defect integrals of the catalog in the comparator 9. The resulting classification output is fed to a further memory 10. After the classification results of one steel pipe 1 are present in the memory 10 that is after a signal from a contactless acting switch is provided via the end of the steel pipe 1 to the calculation provision 11, the calculating provision determines a "total defect" from the classification results of the memory 10, the total defect is compared with a catalog of previously entered total defect sizes as well as with a catalog of periodic defects and are summarized to a test result "good" or "bad" such that the corresponding sorting signals 12, 13 allow a separation of defective steel tubes.

FIG. 2 shows integral areas of signal defects 14, plotted in a diagram, where the amplitude heights A of the ultrasonic defect signals are shown in dependence on the intervals I of the subdivided steel tube 1. The maximum amplitudes here shown by way of the enveloping curve 17 of the ultrasonic defect signals are connected as described with the longitudinal intervals I to display defect integrals if disposed above a "floating" defect threshold for the defect signals 18.

It will be understood that each of the elements described above, or two or more together may also find a useful application in other types of system configurations and signal-processing procedures differing from the types described above.

While the invention has been illustrated and described as embodied in the context of an ultrasonic system for defect determination in welding seams of metal pieces, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method for non-destructive testing of metallic material comprising
    testing a welding seam with ultrasonic equipment;
    sensing ultrasonic defect signals according to the pulse-echo method;
    digitizing the ultrasonic defect signals;
    providing a threshold value for comparing the data;
    integrating the digitized signals with signals corresponding to the longitudinal position along the welding seam; and
    comparing the data resulting from said integrating with data from a catalog of classes of defects.
2. The method of non-destructive testing according to claim 1 further comprising
    marking the metallic material upon exceeding of a threshold value by the defect signal of the ultrasonic data.
3. The method of non-destructive testing according to claim 1 further comprising
    registering separately the exceeding of a threshold value by a defect signal of the ultrasonic data.
4. The method of non-destructive testing according to claim 1 further comprising
    using a magnetic stray flux.
5. The method of non-destructive testing according to claim 1 further comprising
    determining the length over which a defect signal is observed with the successive length over which no defect signal is observed.
6. A method for non-destructive testing of metallic material comprising
    testing a welding seam with ultrasonic equipment;
    sensing ultrasonic defect signals according to the pulse-echo method;
    digitizing the ultrasonic defect signals;
    combining the digitized signals with signals corresponding to longitudinal position along the welding seam;
    producing a defect curve from the data resulting from combining the digitized signals with the signals corresponding to the longitudinal position;
    determining the length over which a defect signal is observed with the successive length over which no defect signal is observed;
    comparing the length, over which a defect signal is observed with the n-fold of the length, over which no defect signal is observed;
    adding the length, over which a defect signal is observed, to the preceding length, over which a defect signal was observed; and
    repeating these steps with the generated total length, over which defects are observed until a larger length, over which no defect signals are observed, occurs, where n can assume the values 0.5, 1, 2, 3, 4, . . . x; where x is an integer.
7. The method of non-destructive testing according to claim 6 further comprising
    correlating the lengths over which defects are observed for uncovering the presence of periodicity along the extension of the metal material; and
    comparing the resulting correlations with a preselected stored catalog of periods and catalog of defects; and
    marking the metallic material according to the classification in the catalog.
8. A method for non-destructive testing of metallic work pieces comprising testing welding seams for defects according to the ultrasonic pulse-echo method and magnetic stray flux method; integrating the digitized signals from the ultrasonic and/or magnetic stray flux testing with signals corresponding to the longitudinal position along the welding seam for determining the defect surface; and comparing the classified defect surface resulting from said integrating with a respective class catalog.
9. A testing apparatus for metallic materials comprising
    sensing means for providing length pulses upon passage over certain length intervals along a metallic material;

a shift register connected to the sensing means for shifting length pulses coming from the sensing means;

an electrically activated ultrasonic transducer coupled to the metallic material;

an ultrasonic receiver connected to the transducer for receiving ultrasonic signals;

an analog-digital converter connected to the ultrasonic receiver;

a peak signal storage connected to the analog digital converter;

a digital processor connected to the peak signal storage and to the shift register for summing products of signal strength times covered corresponding length interval to provide defect integrals;

a comparator connected to the digital processor for comparing defect integrals with preselected values; and a memory connected to the comparator.

10. The testing apparatus for metallic materials according to claim 9 wherein the sensing means is a sensing wheel.

11. The testing apparatus for metallic materials according to claim 9 further comprising a calculating provision connected to the memory.

* * * * *